United States Patent [19]

Grimes

[11] 4,216,769
[45] Aug. 12, 1980

[54] BI-FLOW NASAL CUP

[76] Inventor: Jerry L. Grimes, 1798 N. Gareg Ave., Pomona, Calif. 91767

[21] Appl. No.: 947,005

[22] Filed: Sep. 29, 1978

[51] Int. Cl.$^2$ .......................................... A61M 16/00
[52] U.S. Cl. ........................... 128/207.13; 128/205.25
[58] Field of Search ............... 128/140 N, 140 R, 195, 128/206, 198, 187

[56] References Cited

U.S. PATENT DOCUMENTS

| | | | |
|---|---|---|---|
| 406,118 | 7/1889 | Welch | 128/198 |
| 810,769 | 1/1906 | Jones | 128/209 |
| 1,206,045 | 11/1916 | Smith | 128/206 |
| 1,740,083 | 12/1929 | Galvin | 128/198 |
| 2,292,568 | 8/1942 | Kanter et al. | 128/206 |
| 2,295,321 | 9/1942 | Anderson | 128/198 |
| 2,663,297 | 12/1953 | Turnberg | 128/206 |
| 3,295,521 | 1/1967 | Balch | 128/205 |
| 3,682,171 | 8/1972 | Dali et al. | 128/206 |
| 3,889,671 | 6/1975 | Baker | 128/206 |
| 4,106,505 | 8/1978 | Salter et al. | 128/DIG. 26 |

*Primary Examiner*—Henry J. Recla
*Attorney, Agent, or Firm*—Fishburn, Gold & Litman

[57] ABSTRACT

A bi-flow nasal inhalation cup for mixing oxygen and ambient air includes a crescent shaped cup member or open top receptacle having a recessed pocket in a downwardly sloping collecting floor. A curved inner wall extends above and below a cup floor inner margin and is contoured to gently engage the upper lip of a patient. Opposite wing portions extend outwardly from the inner wall and conform to facial portions laterally of the nose. A substantially vertical outer wall merges with the cup floor and the inner wall and has a center portion which extends above the inner wall and merges with diverging opposite straight arm portions. A pair of cannula inlets respectively extend tangentially through the arm sections and project generally radially outwardly and at an upward angle toward the patient's face. Tubes or cannula are fitted into the inlets and extend toward the patient's face with each tube or cannula having a curve for draping over the patient's ears and supporting the cup member thereby. When worn, the outer wall of the cup is spaced from the patient's nose and permits a flow of ambient air onto the collecting floor which mixes with oxygen for breathing by the patient. The nasal cup is preferably a one piece, injection molded, plastic item designed for low cost, single patient use.

3 Claims, 2 Drawing Figures

U.S. Patent  Aug. 12, 1980  4,216,769
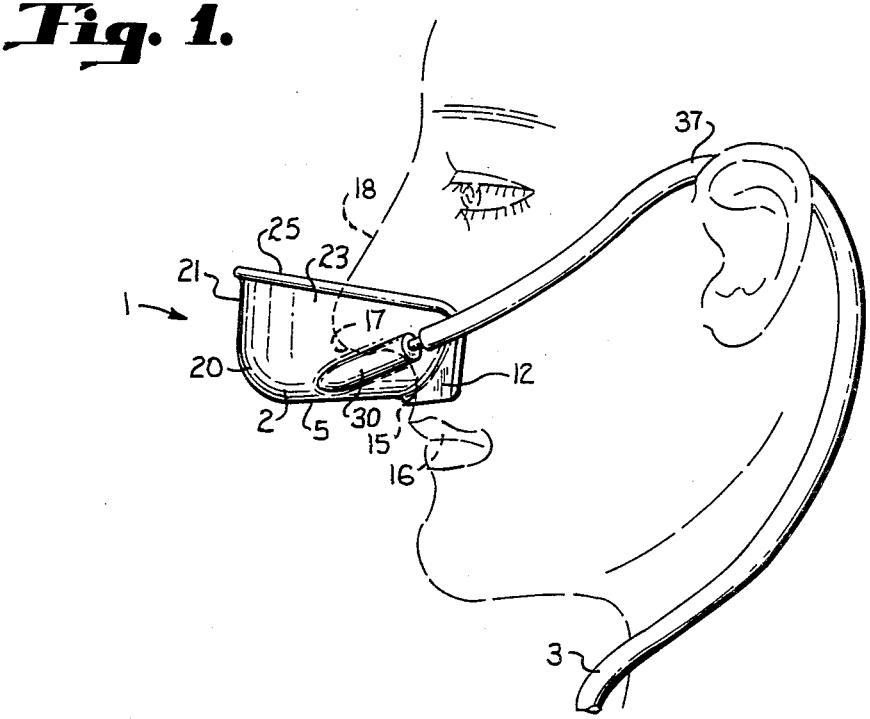
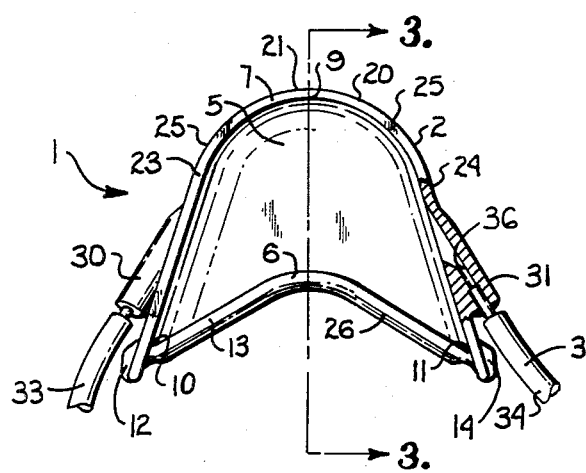
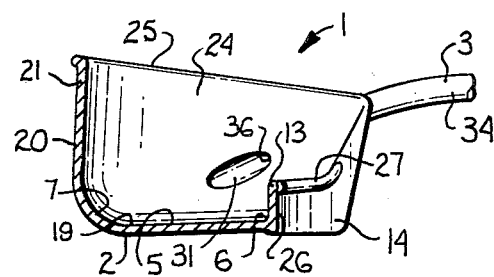

BI-FLOW NASAL CUP

This invention relates to an improved nasal inhalation cup and, in particular, to a disposable single patient use bi-flow inhalation cup mixing delivered oxygen and ambient air. In the treatment of respiratory system disorders, oxygen is often administered by oralpharyngeal oxygen catheters inserted into the nares or nostrils, so that the tip of the catheter is located slightly past the uvula. Such catheters normally have a relatively limited flow range of about five liters per minute and can be irritating to the nostrils. In other instances, oxygen masks covering the patient's mouth and nose are used, however these tend to be restrictive and prevent the patient from conversing, eating and drinking in a normal manner.

Additionally, the administration of pure oxygen tends to dry the nares and upper respiratory areas, thereby promoting infections and necessitating that a humidifier be interposed in the line between the oxygen source and the patient.

The principal objects of the present invention are: to provide a bi-flow inhalation cup for supplying oxygen to a patient that eliminates the disadvantages of prior devices as stated above; to provide such an inhalation cup with inlets of oxygen and ambient air in a manner to mix same for supply to a patient; to provide such an inhalation cup for use with conventional oxygen carrying cannulas with connections substantially tangentially of the cup; to provide such an inhalation cup for supplying oxygen to a patient without tending to dry the nares or produce discomfort; to provide such an inhalation cup which may be used by patients with noses of various shapes; to provide such an inhalation cup which is lightweight and comfortable for wear; to provide an inhalation cup which is comprised of hypo-allergenic material; and to provide such an inhalation cup which is relatively inexpensive and intended for single patient use, sturdy and efficient in use, and particularly well adapted for the intended purpose.

Other objects and advantages of this invention will become apparent from the following description taken in connection with the accompanying drawings wherein are set forth, by way of illustration and example, certain embodiments of this invention.

FIG. 1 is a side elevational view of a nasal inhalation cup embodying the present invention and illustrating a manner of wearing same by a patient.

FIG. 2 is a top plan view of the inhalation cup.

FIG. 3 is a cross-sectional view of the inhalation cup taken along lines 3—3, FIG. 2.

Referring to the drawings in more detail:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a nasal inhalation cup embodying the present invention. The apparatus 1 includes a cup member 2 having a portion engaging a patient's upper lip and an outer wall defining an open top receptacle surrounding and spaced from a patient's nose for entry of air and oxygen conduits or cannulas 3 delivering oxygen to the cup 2 for mixture with the air and breathing of the mixture by the patient.

The illustrated cup member 2 is generally crescent shaped when viewed from the top or bottom, FIG. 2, and has a recessed, bottom or collecting floor 5 which slopes downwardly from an inner margin 6 toward an outer margin 7. Each of the arched margins 6 and 7, when viewed by the patient, FIG. 1, is in the shape of an inverted "U" with the outer margin 7 of substantially greater curvature or radius than the inner margin 6. The outer margin 7 has a smooth apex area 9 and the margins 6 and 7 join at corners 10 and 11.

A substantially vertical, curved inner wall 13 merges with the inner arched margin 6 and extends above and below the collecting floor 5. The inner wall 13 is contoured to accord with the inner arched margin 6 and conform to the shape of the upper lip area 15 of a patient. Side wing portions 12 and 14 extend outwardly of the corners 10 and 11 and are adapted to gently engage facial portions of the wearer above the upper labia 16 and laterally of the nose 17. The inner wall 13 has a vertical dimension generally less than the vertical breath of the person's upper lip area 15 between the upper labia 16 and the bottom of the nose 17.

A substantially vertical, curved outer wall 20 with an arched center portion 21 merges with the outer margin 7 and extends above the inner wall 13 and above the level of the bottom of the nose 17, FIG. 1. Diverging opposite arm portions 23 and 24 merge with the center portion 21 at 25 and curve downwardly at the corners 10 and 11 to merge with the inner wall 13 and the side wind portions 12 and 14. The downwardly sloping collecting floor 5 cooperates with the outer wall 20 to form a recessed pocket or chamber 19 with the lowest portion thereof adjacent the marginal apex area 9 and the center portion 21. In the illustrated example, the inner wall 13 and the outer wall 20 are integrally formed with the collecting floor 5, however it will be appreciated that the walls 15 and 20 can be formed separately from the floor 5 and then connected thereto. The outer wall 20, and particularly the arched center portion 21 thereof, is spaced from the patient's nose 18 when the inner wall 13 rests upon the upper lip area 15, thereby permitting ambient air to flow downwardly onto the recessed collecting floor 5 for breathing by a patient.

In the illustrated example, an elongate pad 26 in the form of a bead or welt is engaged with the surface of the inner wall 13, as by gluing, bonding, or the like and provides a cushion between the upper lip area 15 and the inner wall 13. Preferably, the pad 26 projects slightly outwardly for slip-free engagement with the skin surface of the patient's upper lip area 15. To rest gently upon the sensitive upper lip area 15 and not irritate same, it is preferred that the pad 26 be relatively soft and have a non-sticky outer surface.

A pair of oxygen conduits or cannula inlets 30 and 31 respectively extend through the arm portions 23 and 24 and project generally radially outwardly and at a slight upward angle toward the patient's face for insertion of the cannulas 3. Left and right cannulas 33 and 34 are inserted into the inlets 30 and 31 by pressing and twisting therein for a tight, leakfree fit. Cannula ends 36 respectively extend within the inlets 30 and 31 a sufficient distance for secure retention. The cannula inlets are directed substantially tangentially of the receptacle and located near the bottom thereof, providing a whirling flow facilitating a turbulence which aids the mixture thereof with air entering therein.

For connecting the cup member 2 to the patient's face, the cannulas 3 have curved portions 37 which drape or hook over the ears and thereby support the cup member 2. Other holding means, such as headbands or the like may be substituted for the curved portions 37 as desired.

The nasal inhalation cup 1 illustrated is preferably of a synthetic resin having some flexibility for the inner wall 13 and wing portions 12 and 14 to conform the shape of the patient's upper lip area and face portions laterally of the nose. This flexibility makes the structure adaptable to different facial contours and comfortable to wear. Also, the nasal inhalation cup 1 is of such shape that it may be made in one piece by injection molding at a relatively low per unit cost so as to be inexpensive and hence purposefully disposable after use by a single patient.

In the use of the nasal inhalation cup 1, the cannulas 3 are first connected to respective inlets 30 and 31 and then the cup member 2 is positioned underlying the patient's nose with the pad 26 resting gently against the upper lip area 15. The curved portions 37 of the cannulas 3 are draped over the ears to support the inhalation cup 1 in proper position for breathing. The oxygen flows through the inlets 30 and 31, and, since the oxygen is slightly heavier than the surrounding air, it collects in the recessed pocket or chamber 19 of the floor 5 and tends to remain there. A substantial portion of the cup member 2 is open to the ambient air or atmosphere and upon inhalation, a mixture, or bi-flow, of oxygen and ambient air is drawn through the nose 18 and into the patient's respiratory system. The oxygen source may be adjusted to provide a slight positive flow of oxygen into the nasal inhalation cup 1 and the patient may inhale up to ten to twelve liters per minute of oxygen in this manner. The substantial opening of the cup member 2 surrounding the patient's nose 18 permits excess oxygen to overflow from the outer wall 20 and not be forced into the patient's lungs. If the patient exhales through the nose, which is not recommended, expended air and oxygen are simply vented outwardly over the cup outer wall 20.

It will be appreciated that the nasal inhalation cup 1 is relatively easy for a patient to handle and does not tend to be restrictive during use, allowing the patient to freely converse and eat or drink during the administration of oxygen. Moreover, because ambient air is mixed with oxygen, natural moisture of the ambient air is utilized and humidification of the oxygen source may be unnecessary. The nasal inhalation cup 1 rests comfortably upon the upper lip area 15 and is preferably of such lightweight and conforming shape such that little or no discomfort is felt.

It is to be understood that while one form of this invention has been illustrated and described, it is not to be limited to the specific form or arrangement of parts herein described and shown except insofar as such limitations are included in the following claims.

What is claimed and desired to secure by Letters Patent is:

1. A bi-flow nasal inhalation cup comprising:
  (a) a generally crescent shaped cup member of lightweight, relatively flexible plastic material having a collecting floor having inner and outer laterally arched margins;
  (b) an upright, curved inner wall connected to said inner margin and having sidewardly flaring wing portions contoured to smoothly and gently rest against the upper lip area of a patient;
  (c) an upright, curved outer wall connected to said outer margin and having a vertically arched center portion extending above said inner wall and merging into opposite arm portions smoothly diverging therefrom, said outer wall being spaced from the patient's face when said inner wall rests upon the patient's upper lip area and cooperating with the inner wall and collecting floor to define an open top receptacle for permitting flow of ambient air onto said collecting floor;
  (d) opposed cannula inlets extending generally tangentially through opposite arm portions of said outerwall and pointing generally downwardly toward said collecting floor for connection to an oxygen gas carrying cannula for turbulent, swirling flow of oxygen gas into the receptacle for well integrated mixing with air coming over said outer wall, thereby providing such mixture adjacent a patient's nostrils for inhalation by the patient; and
  (e) means connecting said cup to a patient's face.

2. The inhalation cup set forth in claim 1 wherein:
  (a) said cannula inlets respectively extend through said arm sections and have outer ends projecting generally radially outwardly and angularly upwardly toward the patient's face.

3. The inhalation cup set forth in claim 2 wherein:
  (a) said means connecting said cup member to a patient's face includes a pair of cannulas respectively connected to said cannula inlets and extending toward the patient's face; and
  (b) said cannulas respectively have a curved portion for draping said cannulas over a patient's ears and thereby supporting said cup member.

* * * * *